United States Patent
Sterry (10) Patent No.: US 11,039,824 B1
(45) Date of Patent: Jun. 22, 2021

(54) SURGICAL RETRACTOR DEVICE

(71) Applicant: Thomas P. Sterry, New York, NY (US)

(72) Inventor: Thomas P. Sterry, New York, NY (US)

( * ) Notice: Subject to any disclaimer, the term of this patent is extended or adjusted under 35 U.S.C. 154(b) by 0 days.

(21) Appl. No.: 16/002,456

(22) Filed: Jun. 7, 2018

(51) Int. Cl.
*A61B 17/02* (2006.01)
*A61B 17/00* (2006.01)

(52) U.S. Cl.
CPC ..... *A61B 17/0281* (2013.01); *A61B 2017/00424* (2013.01)

(58) Field of Classification Search
CPC ............. A61B 17/0281; A61B 1/32; A61B 2017/00424
See application file for complete search history.

(56) References Cited

U.S. PATENT DOCUMENTS

| | | | | |
|---|---|---|---|---|
| 2,829,649 A * | 4/1958 | Glenner | ................. | A61B 17/42 606/201 |
| 4,226,228 A * | 10/1980 | Shin | ........................ | A61B 1/32 600/206 |
| 4,232,660 A * | 11/1980 | Coles | ..................... | A61B 17/02 600/205 |
| 4,934,352 A * | 6/1990 | Sullivan, Jr. | ............ | A61B 17/02 600/213 |
| 5,379,758 A | 1/1995 | Snyder | | |
| 5,398,671 A * | 3/1995 | Ortiz | .................. | A61B 17/0281 600/204 |
| 5,431,153 A * | 7/1995 | Lee | .................... | A61B 17/0218 600/183 |
| 5,558,621 A | 9/1996 | Heil | | |
| 5,755,660 A | 5/1998 | Tyagi | | |
| 5,800,346 A | 9/1998 | Adams | | |
| 5,846,192 A | 12/1998 | Teixido | | |
| 5,882,299 A * | 3/1999 | Rastegar | ............ | A61B 17/0281 600/232 |
| 6,033,425 A * | 3/2000 | Looney | ............. | A61B 17/0206 600/232 |
| 6,193,651 B1 | 2/2001 | DeFonzo | | |
| 6,354,994 B1 * | 3/2002 | Rullo | ..................... | A61B 17/02 600/217 |
| 6,428,472 B1 | 8/2002 | Haas | | |
| 7,951,077 B2 * | 5/2011 | Sayeg | .................... | A61B 17/02 600/210 |
| 8,460,185 B2 | 6/2013 | Epstein et al. | | |
| 8,529,444 B2 * | 9/2013 | Hale | ...................... | A61B 17/02 248/615 |

(Continued)

OTHER PUBLICATIONS

ASSI Epstein Abdominoplasty Retractor, Jun. 6, 2017, http://www.accuratesurgical.com/products/plastic-surgery/product/2398-epstein-abdominoplasty-retractor.

*Primary Examiner* — David W Bates
(74) *Attorney, Agent, or Firm* — Collard & Roe, P.C.

(57) ABSTRACT

A surgical retractor for abdominoplasty is disclosed. The retractor has a blade which has a pair of wings disposed below a spine which form a surgical window. The pair of wings form a substantially bell curve shape below the spine of the blade. The pair of wings have outer edges which are curved, and which allow the surgical retractor to be rocked by a user to adjust the surgical window. The retractor has a handle which has a grip portion substantially parallel to the spine of the blade and which provides a more ergonomic grip and greater control.

13 Claims, 4 Drawing Sheets

(56) References Cited

U.S. PATENT DOCUMENTS

| | | | |
|---|---|---|---|
| 8,684,577 B2* | 4/2014 | Vayser | A61B 1/07 |
| | | | 362/573 |
| 2004/0143163 A1 | 7/2004 | Palmer et al. | |
| 2006/0122580 A1* | 6/2006 | Dannan | A61B 17/3403 |
| | | | 606/1 |
| 2009/0192511 A1 | 7/2009 | Haffenreffer | |
| 2011/0190591 A1 | 8/2011 | Palmer et al. | |
| 2014/0031630 A1* | 1/2014 | Nguyen | A61B 17/02 |
| | | | 600/204 |
| 2020/0015801 A1* | 1/2020 | Sauer | A61B 17/0281 |

\* cited by examiner

SURGICAL RETRACTOR DEVICE

BACKGROUND OF THE INVENTION

Field of the Invention

The present invention relates to a surgical retractor, and more particularly, a SURGICAL RETRACTOR DEVICE suitable for use in abdominoplasty, also known as "tummy tuck" surgery.

Description of the Prior Art

Numerous innovations for surgical retractors have been provided in the prior art that will be described. Even though these innovations may be suitable for the specific individual purposes to which they address, however, they differ from the present invention.

A FIRST EXAMPLE, U.S. Pat. No. 4,934,352, Published/Issued on Jun. 19, 1990, to Sullivan, Jr. teaches a surgical retractor designed to retract large areas in abdominal cavity surgery. The retractor is comprised of a handle that may be used interchangeably with different sized retractor blades to suit a particular surgical purpose. The handle is disposed or can be adjusted to be disposed at an angle of generally 90° with respect to the retractor blade to afford an easier and more comfortable hold and pull than that experienced with any other designed retractor. The retractor may be fitted with one large retractor blade where previously two or three small retractors were used, and is, therefore, useful in small hospitals in major surgery such as aneurysms, Whipples and node dissections.

A SECOND EXAMPLE, U.S. Pat. No. 5,379,758, Published/Issued on Jan. 10, 1995, to Snyder teaches a retractor has a blade which is in contact with a surgical wound. A handle has one end supported by the blade and extends substantially normal thereto, and has an opposite free end. A brace plate is attached to the free end of the handle and fits against the user's forearm to stabilize the retractor. A hand grip is attached to the handle between the blade and the brace plate. The arrangement is such that a fulcrum is created at the attachment between the hand grip and the handle, whereby the larger and stronger muscles of the user are available with a mechanical advantage to control the retractor. The blade may assume a variety of configurations and the blade, hand grip and brace plate are pivotable in a variety of planes relative to the plane of the handle.

A THIRD EXAMPLE, U.S. Pat. No. 5,558,621, Published/Issued on Sep. 24, 1996, to Heil teaches a handle for a surgical retractor comprises a central, elongated rod member and two gripping and leverage crossbars that intersect the rod member. The handle is useful with a variety of retractor blades for increasing comfort, decreasing fatigue, and improving leverage over a retractor blade.

A FOURTH EXAMPLE, U.S. Pat. No. 5,755,660, Published/Issued on May 26, 1998, to Tyagi teaches an apparatus and method of performing a cholecystectomy procedure through a 3-centimeter incision in the minimum stress triangle through the falciform ligament which provides for direct vertical view of the biliary ducts during dissection. Special tools are provided for this type and other types of surgical operations including obtuse-angled retractors having optionally fixed thereto lighting devices and/or suction devices.

A FIFTH EXAMPLE, U.S. Pat. No. 5,800,346, Published/Issued on Sep. 1, 1998, to Adams teaches a surgical retractor holder includes a length of pliant material having opposed fastening end areas at which hook elements or the like are located for engaging opposite sides of a surgical table. Open ended pockets are provided along the length of the material for receiving the proximal end of a retractor handle to secure the handle in position when the length of material is fixedly secured to a surgical table across a surgery patient. The retractor holder enables the retractor to be secured in position without the need for manipulation by a surgical assistant.

A SIXTH EXAMPLE, U.S. Pat. No. 5,846,192, Published/Issued on Dec. 8, 1998, to Teixido teaches a surgical retractor made of polymeric material is provided for use especially with electric scalpels.

A SEVENTH EXAMPLE, U.S. Pat. No. 6,193,651, Published/Issued on Feb. 27, 2001, to DeFonzo teaches a surgical retractor comprising a base adapted to lie on the patient's skin, a handle slidably mounted with respect to the base, a tissue retracting blade extending from the handle, and a locking member movable from at least a first position to a second position to retain the tissue retracting blade in a selected position. A light guide illuminates the surgical site during use. An angle adapter can be mounted to the base to increase the angle of the tissue retracting blade with respect to the tissue. A method for accessing the saphenous vein to facilitate harvesting the vein is also disclosed comprising the steps of making a small incision in the leg of a patient, positioning a retractor on a patient's leg such that a retractor blade extends into the incision and a base lies on the surface of the patient's leg and pulling the retractor blade away from the patient to lift the tissue away from the underlying saphenous vein.

AN EIGHTH EXAMPLE, U.S. Pat. No. 6,428,472, Published/Issued on Aug. 6, 2002, to Haas teaches a retractor device for use in surgical procedures is disclosed. The retractor has a handle element that is held by a surgeon. The handle element has a first end and a second end. At least a portion of the handle element between the first end and the second end is fabricated from a malleable material. The malleable material enables the relative position between the first end of the handle element and the second end of the handle element to be selectively adjusted by hand. A rigid retractor blade extends from the first end of the handle element. By altering the shape of the handle element, the orientation of the rigid retractor blade can be selectively altered. As such, a surgeon can selectively change the shape of the retractor without sacrificing the strength of the contact blade portion of the retractor.

A NINTH EXAMPLE, U.S. Pat. No. 8,460,185, Published/Issued on Jun. 11, 2013, to Epstein, et al. teaches a surgical retractor assembly that utilizes a tubular shaft and a connection nub. A pivot joint connects one end of the tubular shaft to the connection nub. The pivot joint enables the connection nub to move relative the tubular shaft along a path that is coplanar to the axis of the tubular shaft. Together, the tubular shaft and the connection nub create an elongated element that can be introduced into a small incision. A retractor blade is provided. A bearing joint extends from the retractor blade. The retractor blade and bearing joint are introduced into a surgical site independent of the elongated element. Within the surgical site, the connection nub interconnects with the bearing joint, therein joining the retractor blade to the tubular shaft and a handle.

A TENTH EXAMPLE, U.S. Patent Office Document No. 20040143163, Published/Issued on Jul. 22, 2004, to Palmer, et al. teaches an endoscopic retractor includes a tube having a proximal end and a distal end with a push rod extending therethrough. The proximal ends of the push rod is provided with a threaded portion. A rotatable handle is coupled to the proximal end of the tube and threadably engages the threaded portion of the push rod such that rotation of the handle causes a translation of the push rod. The distal end of the tube is provided with a clevis through which the distal end of the push rod extends. A multi-segment canopy is coupled to the clevis and the push rod via an articulate linkage. Translation of the push rod in the distal direction causes the canopy to be moved from a starting substantially cylindrical configuration with its axis nearly collinear with the axis of the tube to an opened quasi-planar configuration. Further translation of the push rod in the distal direction causes the quasi-planar canopy to be rotated in the clevis to an angle of approximately ninety degrees relative to the axis of the tube.

AN ELEVENTH EXAMPLE, U.S. Patent Office Document No. 20090192511, Published/Issued on Jul. 30, 2009, to Haffenreffer teaches orthopedic procedures, such as total hip replacement and/or other surgical procedures, involve the retraction and distraction of bone and tissue in order to reduce prosthesis components, such as a femoral head prosthesis, into place during surgery and to perform other surgical techniques, such as reaming of the acetabulum. An instrument handle that allows for enhanced control of surgical instruments and other tools that involve the application of directional force includes a grip, an extension arm and a support brace that is configured to contact a user's forearm during a surgical procedure. A multiple-tool receptor may also be included that allows for the removable and interchangeable use of tools in connection with the instrument handle. The system described herein allows for deep distraction without angulation using larger muscles or even one's body.

A TWELFTH EXAMPLE, U.S. Patent Office Document No. 20110190591, Published/Issued on Aug. 4, 2011, to Palmer, et al. teaches a surgical retractor that can be manipulated with only a digit of a single hand. The surgical retractor includes a shaft, which may be cylindrical, with a finger member attached to one side. The finger member may be an arc segment properly sized to keep a digit next to the shaft. Attached to one end of the shaft is a rake head. The rake head consists of three segments attached to one another, the first of which is attached to the shaft. The final segment has a concavity formed upon it to allow another instrument access beneath the surgical retractor. The method of using the surgical retractor is also disclosed.

A THIRTEENTH EXAMPLE, the ASSI EPSTEIN ABDOMINOPLASTY RETRACTOR first retrieved from the website accuratesurgical.com on Jun. 6, 2017 illustrates a retractor of the type commonly used for abdominoplasty by surgeons today. A substantial replica of this is included in the present application as FIG. 2 and is used for comparison of the advantages of the present invention.

It is apparent now that numerous innovations for surgical retractors have been provided in the prior art that adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide a SURGICAL RETRACTOR DEVICE that avoids the disadvantages of the prior art.

ANOTHER OBJECT of the present invention is to provide a SURGICAL RETRACTOR DEVICE that is simple and inexpensive to manufacture.

STILL ANOTHER OBJECT of the present invention is to provide a SURGICAL RETRACTOR DEVICE that is simple to use.

BRIEFLY STATED, STILL YET ANOTHER OBJECT of the present invention is to provide a SURGICAL RETRACTOR DEVICE that is more ergonomic than prior devices and is self-supporting.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWINGS

The figures of the drawings are briefly described as follows.

A MARSHALING OF REFERENCE NUMERALS UTILIZED IN THE DRAWINGS 10 surgical retractor
12 blade
14 handle
16 proximal end of blade 12
18 distal end of blade 12
20 pair of wings of blade 12
22 spine of blade 12
23 substantially bell curve shape below spine 22 of blade 12
24 common point of pair of wings 20 of blade 12
25 surgical window
26 outer edges of pair of wings 20 of blade 12
28 tangental angle of curve of outer edges 26 of pair of wings 20 of blade 12
30 flat portion of outer edges 26 of pair of wings 20 of blade 12
32 top surface of flat portion 30 of outer edges 26 of pair of wings 20 of blade 12
34 bottom surface of flat portion 30 of outer edges 26 of pair of wings 20 of blade 12
36 texture of top surface 32 of flat portion 30 of outer edges 26 of pair of wings 20 of blade 12
38 width of blade 12
40 width of surgical window 25
42 height of surgical window 25
44 arm portion of handle 14
46 grip portion of handle 14

48 first curve of arm portion 44 of handle 14
50 second curve of arm portion 44 of handle 14
100 prior art retractor
102 edge of blade 104 of prior art retractor 100
104 blade of prior art retractor 100
106 serrated edge 102 of prior art retractor 100

DETAILED DESCRIPTION OF THE
PREFERRED EMBODIMENT

Figure 1:
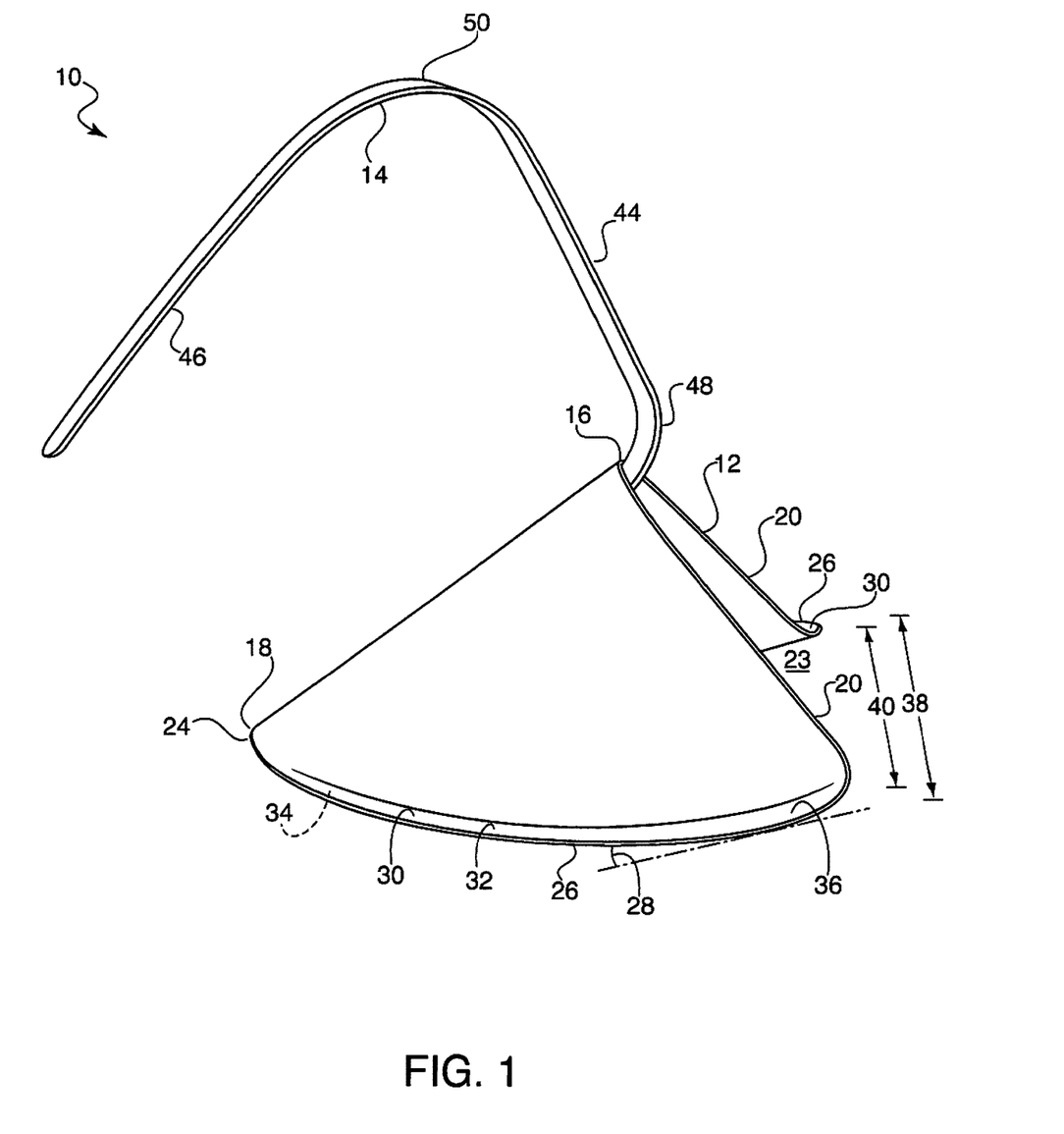
FIG. 1 is a diagrammatic perspective view of an embodiment of the SURGICAL RETRACTOR DEVICE per se.

Referring now to the figures, in which like numerals indicate like parts, and particularly to FIG. 1, disclosed is a surgical retractor 10 which includes:
 a) a blade 12; and
 b) a handle 14.
The blade 12 has a proximal end 16 and a distal end 18. The blade 12 also has a pair of wings 20. The blade 12 also has a spine 22. Each of said pair of wings 20 extends from the spine 22. The spine 22 extends from the proximal end 16 to the distal end 18 of the blade 12. The handle 14 is connected to the blade 12 at the spine 22. The pair of wings 20 are disposed at least partially below the spine 22.

Figure 3A:
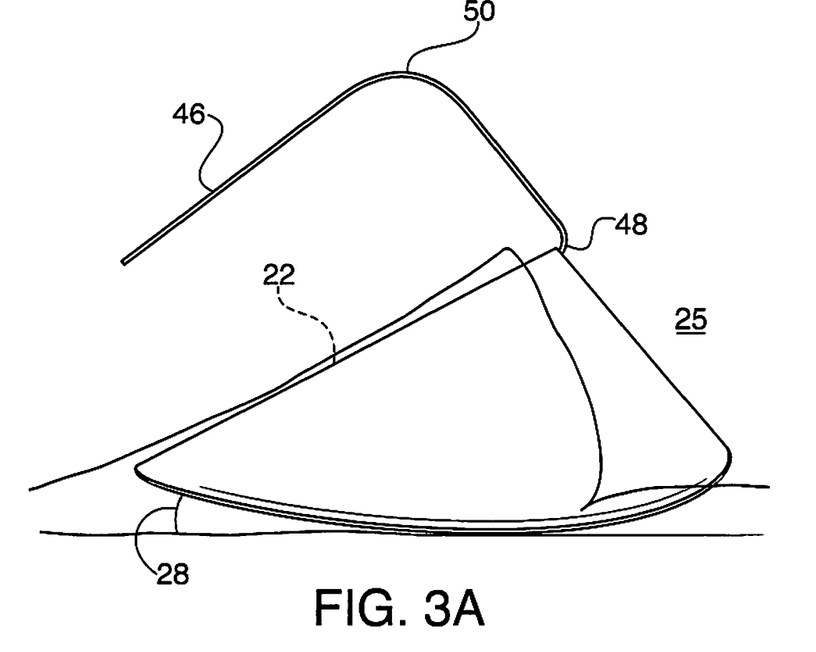
FIG. 3A is a diagrammatic side elevational view illustrating he device being inserted under a flap of skin in the torso of a human being.
Figure 3B:
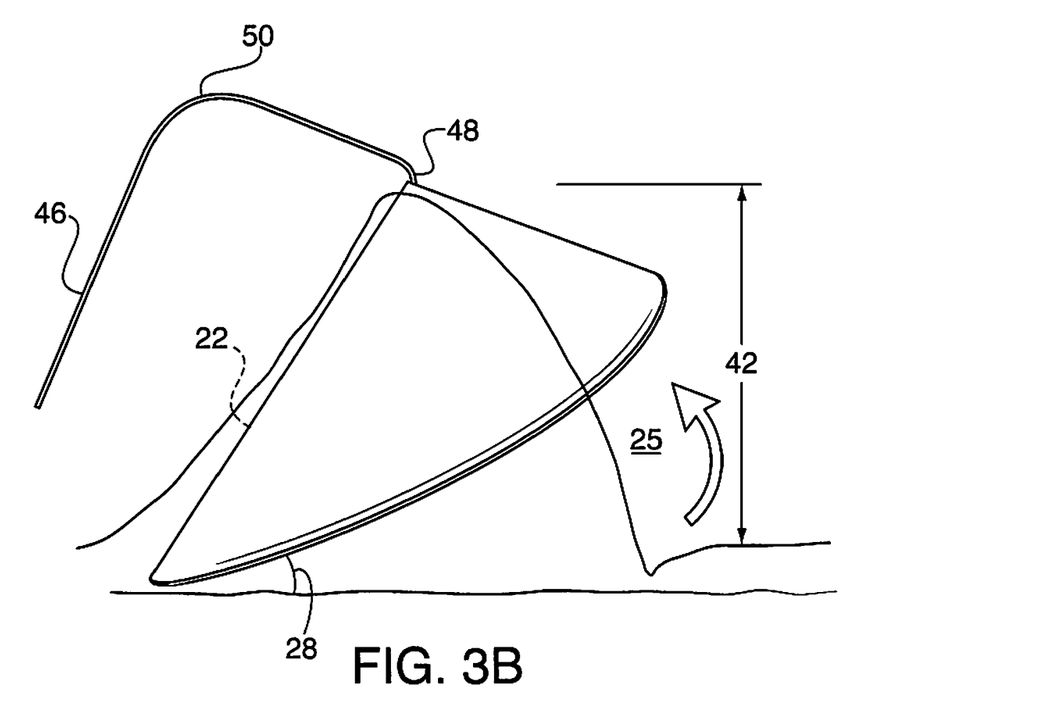
FIG. 3B is a diagrammatic side elevational view illustrating he device being rocked to lift skin of the torso.

This structure permits several advantages. By disposing the pair of wings 20 at least partially below the spine 22, and having the handle 14 connected to the blade 12 at the spine, the retractor 10 uses the spine as a central structural support, with the disposition of the pair of wings 20 at least partially below the spine 22 ensuring that the weight of flesh on the retractor (as illustrated in FIGS. 3A, 3B, and 4) does not deform the pair of wings 20.

Detailed Description of the Blade 12

Figure 4:
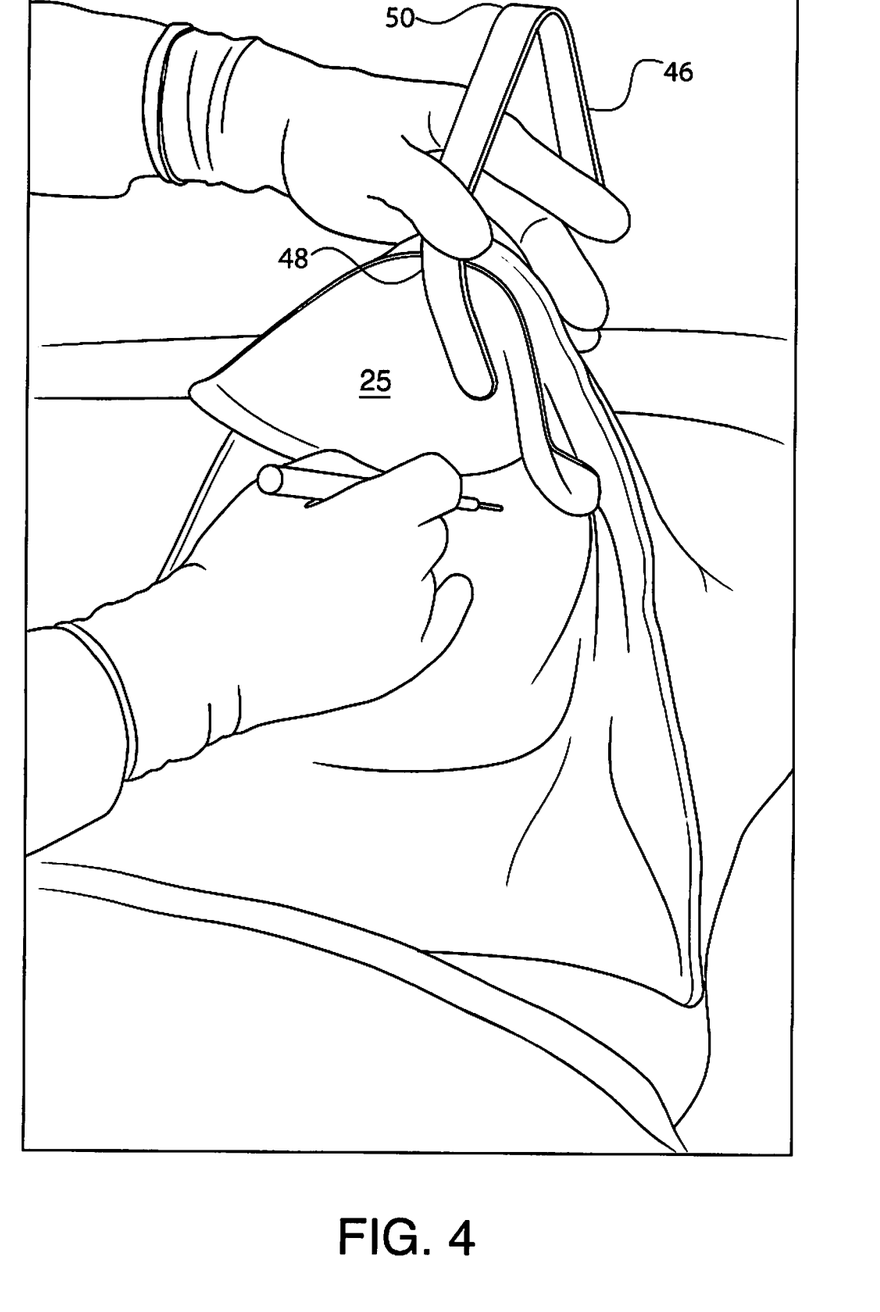
FIG. 4 a diagrammatic perspective view illustrating the device being utilized to allow ample access to the area of the torso normally under the lifted skin so that appropriate surgery may be preformed.

In the preferred construction, and as most clearly illustrated in FIG. 4, the pair of wings 20 are mirror images of one another. This simplifies construction as well as ensuring that the spine 22 is centered in the retractor 10, which enhances structural strength.

Further in the preferred construction, the pair of wings 20 are disposed at least partially below the spine 22 such that at the proximal end 16 of the blade 12 they form a substantially bell curve shape 23 below the spine 22. This substantially bell curve shape mirrors the manner in which flesh naturally falls when held up from a central point, and provides even support for a patient's flesh when in use, reducing stretching and strain on the flesh, as well as preventing slippage by having relatively even gravitational and tension force applied by the flesh on the blade 12 of the retractor 10.

As illustrated in FIG. 1, the pair of wings 20 come to a common point 24. The common point 24 is at the distal end 18 of the blade 12. The blade 12 is for forming a surgical window 25 extending from the substantially bell curve shape 12 below the proximal end 16 of the blade 12 to the common point 24 of the blade 12.

Figure 2:
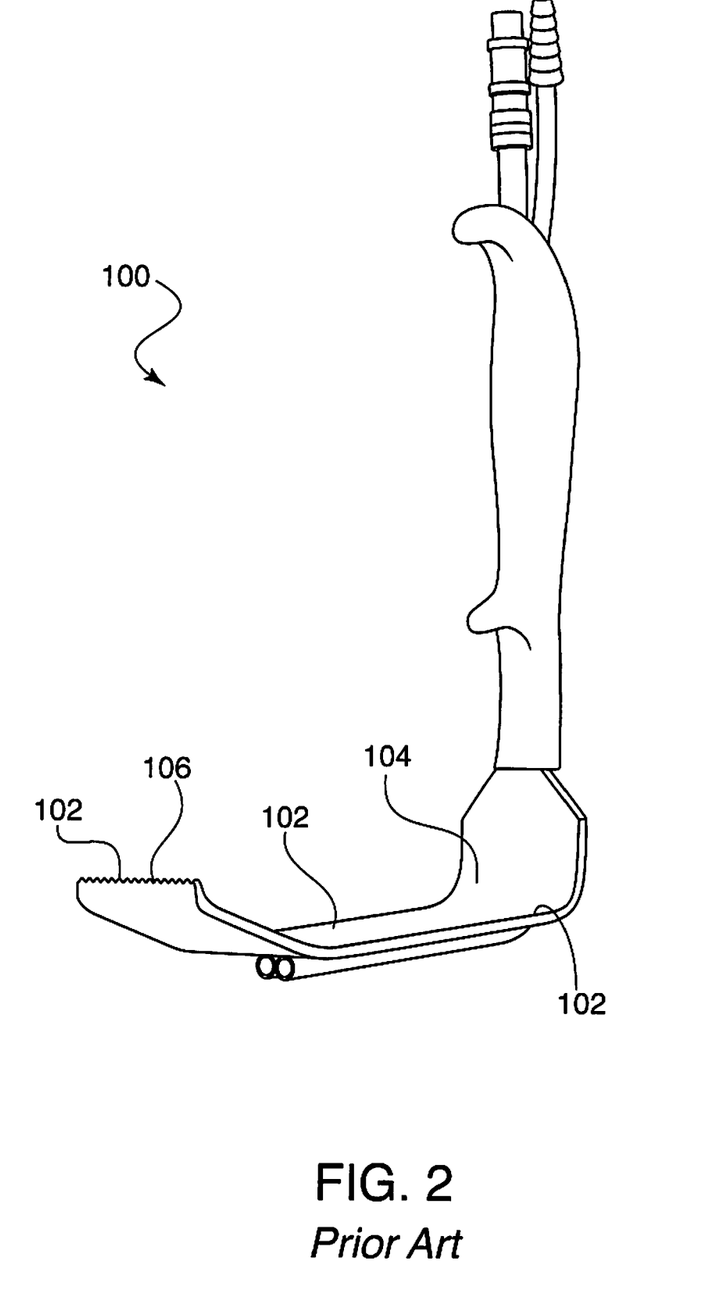
FIG. 2 is a diagrammatic perspective view of a PRIOR ART device which is a classic retractor with a 90 Degree Angle.

In this manner, the retractor can be contrasted against prior art retractors 100 like those illustrated in FIG. 2. Prior art retractors typically used have an end point which is not the edge of the surgical window, since they are designed to have flesh fall away from them forming the surgical window around the edges 102 the blade 104 of the prior art retractor. In this manner, prior art retractors therefore require a user to continually provide upward holding pressure, and form a surgical window whose length varies with how much upward pressure is applied. The present invention overcomes that by providing a surgical window whose length is kept the same by the passive operation of the blade 12 of the retractor 10.

In order to allow adjustment of the surgical window 25 each of said pair of wings 20 has an outer edge 26. Each outer edge 26 of each wing 20 is curved. The curve of each outer edge 26 of each wing 20 is for cooperating with one another to allow the surgical retractor 10 to rock on the outer edges 26 of the pair of wings 20. This rocking allows the surgical window 25 to be adjusted while the surgical retractor 10 remains self-supporting.

Each curve of the outer edge 26 of each wing 20 has a tangental angle 28. The tangental angle 28 of the curve of the outer edge 26 of each wing 20 is the same as the other wing 20. The rocking of the surgical retractor 10 allows the surgical window 25 to extend below the bell curve shape 23 below the proximal end 16 of the blade 12. The tangental angle 28 of the curve of the outer edge 26 of each wing 20 is at least 15 degrees. The tangental angle 28 of the curve of the outer edge 26 of each wing 20 is at most 45 degrees. This range allows for smooth rocking of the surgical retractor 10 within the dimensions typical of incisions for the preferred surgical uses of the device.

As illustrated in FIGS. 1 and 4, the outer edges 26 of each of the pair of wings 20 has a flat portion 30. The flat portion 30 of each of the pair of wings 20 is for better contacting and gripping the flesh of a patient, and for being captured between the skin and flesh of a patient. The flat portion 30 of each of said pair of wings has a top surface 32 and a bottom surface 34. The top surface 34 of the flat portion 30 of each of the pair of wings 20 has a texture for providing additional grip. This contrasts with prior art retractors which because of their limited areas often use serrated edges 106 which can be more damaging to skin and flesh than the present invention.

In the preferred construction, each of the pair of wings 20 extends entirely below the spine 22 of the blade 12. This allows that the spine 22 is the peak of the blade 12. Further, each of the pair of wings 20 has an outer edge 26. Apart from the outer edge 26 of each of the pair of wings 20, the blade has a substantially smoothed surface without sharp edges. This prevents sharp edges or corners from cutting into flesh as mentioned as an advantage of the present invention.

The blade 12 of the surgical retractor 10 has a width 38. The surgical window 25 has a width 40. The width 38 of the blade 12 is at least as large as the width 40 of the surgical window 25 when the surgical retractor 10 has not been adjusted by rocking. This is most clearly illustrated in FIG. 1. This allows that the blade's 12 width 38 can control the size of the surgical window 25 allowing more precision in use.

Moreover, as illustrated in FIGS. 3A and 3B, the surgical window 25 has a height 42. The height 42 of the surgical window 25 is for being adjusted by rocking of the surgical retractor 10. This allows a surgeon using the surgical retractor 10 to choosably adjust the height 42 of the surgical window 25 while the surgical retractor 10 remains self-supporting.

Detailed Description of the Handle 14

Moving now to the handle 14 of the surgical retractor 10, the handle 14 includes an arm portion 44 and a grip portion 46. The arm portion 44 of the handle 14 has a first curve 48. This is best illustrated in FIGS. 1, 3A, and 3B. This allows that the curve of the handle 14 is not contained in the blade 12 as it would be in the prior art blade 104 seen in FIG. 2.

The first curve 48 of the arm portion 44 of the handle 14 is within the same plane as the spine 22 of the blade 12. This allows that the handle can be used for rocking the surgical retractor as illustrated in FIG. 4 without applying a torque on the blade 12 of the retractor such that it would twist instead of rock.

The first curve 48 of the arm portion 44 of the handle 14 curves upwardly and above the spine 22 of the blade 12. This puts the handle 14 in the most ergonomical position, and deters a user from inserting the blade 12 of the surgical retractor 10 deeper than they should, preventing accidents.

Further to the same end, the first curve 48 of the arm portion 44 of the handle 14 is approximately ninety degrees.

As seen in FIG. 1, the arm portion 44 of the handle 14 has a second curve 50. The second curve 50 is further from the proximal end 16 of the blade 12 than the first curve 48. The second curve 50 is closer to the grip portion 46 of the handle 14 than the first curve 48. As most clearly seen in FIGS. 3A and 3B, the second curve 50 of the arm portion 44 of the handle 14 is approximately ninety degrees. Because of this, the grip portion 46 is substantially parallel to the spine 22 of the blade 12.

This provides numerous ergonomic advantages. It allows a user such as a surgical assistant or nurse to hold the grip portion 46 of the retractor more ergonomically and for longer periods, and allows a user to more precisely control the angle of the rocking of the retractor 10 because it mirrors the movement of the grip portion 46.

Further to the same end, the arm portion 44 of the handle 14 is rigid and suitable for acting as a lever upon the blade 12. The arm portion 44 of the handle 14 is permanently fixed to the blade 12. This prevents miscalibration or separation of parts where infectious material could arise.

To ensure that the surgical retractor 10 is capable of being sterilized in a wet autoclave, the surgical retractor 10 is made entirely of materials capable of withstanding a heat of 121 degrees Celsius without deforming.

To ensure that the surgical retractor 10 is capable of being sterilized in a dry autoclave, the surgical retractor 10 is made entirely of materials capable of withstanding a heat of 170 degrees Celsius without deforming.

It will be understood that each of the elements described above, or two or more together, may also find a useful application in other types of constructions differing from the types described above.

It will be further understood that in this application, the word "blade" has been used in the manner which it is commonly used in respect to parts of surgical tools for holding flesh and skin away from an incision to allow a surgeon to work, and does not imply a cutting edge which would slice.

It will be further understood that the present invention is suitable for inclusion of various accessories such as cameras and lights which are known in the art, and illustrated in FIG. 2 on a prior art device.

While the invention has been illustrated and described as embodiments of a SURGICAL RETRACTOR DEVICE, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A surgical retractor which comprises:
   a) a blade; and
   b) a handle;
   wherein said blade has a proximal end and a distal end;
   wherein said blade has a pair of wings;
   wherein said blade has a spine;
   wherein said spine has a proximal end and a distal end;
   wherein said proximal end and said distal end of said blade coincide with said proximal end and said distal end of said spine, respectively;
   wherein each of said pair of wings depends from said spine;
   wherein said spine extends from said proximal end to said distal end of said blade;
   wherein said handle is connected to said blade at said spine;
   wherein said pair of wings are disposed at least partially below said proximal end of said spine;
   wherein said pair of wings are mirror images of one another;
   wherein said pair of wings are disposed at least partially below said proximal end of said spine such that at said proximal end of said blade said pair of wings form a substantially bell curve shape below said proximal end of said spine;
   wherein said handle comprises an arm portion, a grip portion, a first curve and a second curve;
   wherein said first curve of said handle is within the same plane as said spine of said blade;
   wherein said first curve of said handle curves upwardly and above said proximal end of said spine of said blade;
   wherein said arm portion of said handle extends between said first curve of said handle and said second curve of said handle at approximately ninety degrees to said spine; and
   wherein said grip portion of said handle extends from said second curve of said handle at approximately ninety degrees to said arm portion and substantially parallel to said spine over a distance sufficient for a user to grip said grip portion in use with his or her fingers.

2. The surgical retractor of claim 1 wherein said pair of wings come to a common point;
   wherein said common point is at said distal end of said blade; and
   wherein said blade is for forming a surgical window extending from said substantially bell curve shape below said proximal end of said blade to said common point of said blade.

3. The surgical retractor of claim 2 wherein each of said pair of wings has an outer edge;
   wherein each said outer edge of each said wing is curved; and
   wherein said curve of each said outer edge of each said wing is for cooperating with one another to allow the surgical retractor to rock on said outer edges of said pair of wings.

4. The surgical retractor of claim 3 wherein said rocking of said surgical retractor allows the surgical window to extend below said substantially bell curve shape below said proximal end of said blade.

5. The surgical retractor of claim 3 wherein said outer edges of each of said pair of wings comprises a flat portion;
   wherein said flat portion of each of said pair of wings is for facilitating contacting and gripping the flesh of a patient, and for being captured between the skin and flesh of a patient.

6. The surgical retractor of claim 5 wherein said flat portion of each of said pair of wings has an uppermost surface and a lowermost surface; and
   wherein said an uppermost surface of said flat portion of each of said pair of wings has a texture for providing additional grip of the flesh.

7. The surgical retractor of claim 2 wherein each of said pair of wings extends entirely below said proximal end and said distal end of said spine of said blade.

8. The surgical retractor of claim 7 wherein each of said pair of wings has an outer edge; and
   wherein apart from said outer edge of each of said pair of wings, said blade has a substantially smoothed surface without sharp edges.

9. The surgical retractor of claim 8 wherein said blade has a width defined by a distance from one wing to the other wing at a widest separation therebetween; and
   wherein said surgical window has a width; and
   wherein said width of said blade is at least as large as said width of said surgical window when said surgical retractor has not been adjusted by rocking.

10. The surgical retractor of claim 1 wherein said arm portion of said handle is rigid and suitable for acting as a lever upon said blade.

11. The surgical retractor of claim 10 wherein said arm portion of said handle is permanently fixed to said blade.

12. The surgical retractor of claim 11 wherein said surgical retractor is made entirely of materials capable of withstanding a heat of 121 degrees Celsius without deforming.

13. The surgical retractor of claim 12 wherein said surgical retractor is made entirely of materials capable of withstanding a heat of 170 degrees Celsius without deforming.

* * * * *